United States Patent [19]

Odland

[11] Patent Number: 5,265,593
[45] Date of Patent: Nov. 30, 1993

[54] BALLOON-TIPPED CATHETER VENTILATION SYSTEM AND METHOD FOR USING SAME HAVING RHYTHMICALLY INFLATED AND DEFLATED BALLOON

[76] Inventor: Rick M. Odland, 1358 Knoll Rd., Redlands, Calif. 92373

[21] Appl. No.: 694,928

[22] Filed: May 2, 1991

[51] Int. Cl.⁵ .................. A61M 16/00; A62B 7/00; A62B 9/02
[52] U.S. Cl. .................. 128/204.18; 128/207.15; 128/205.24
[58] Field of Search .................. 128/207.14, 207.15, 128/207.16, 204.18, 204.21, 205.19, 205.23, 205.24, 911, 912, 204.18; 604/93-103

[56] References Cited

U.S. PATENT DOCUMENTS

| | | |
|---|---|---|
| 3,322,126 | 5/1967 | Rusch et al. |
| 3,363,629 | 1/1968 | Kuhn |
| 3,407,817 | 10/1968 | Gallehar, Jr. |
| 3,504,676 | 4/1970 | Lomholt |
| 3,734,100 | 5/1973 | Walker et al. |
| 3,884,242 | 5/1975 | Bazell et al. |
| 3,901,246 | 8/1975 | Wallace |
| 4,018,231 | 4/1977 | Wallace |
| 4,147,170 | 4/1979 | Taylor |
| 4,285,340 | 8/1981 | Gezari et al. ............ 128/207.15 |
| 4,471,775 | 9/1984 | Clair et al. ............ 128/207.15 |
| 4,565,194 | 1/1986 | Weeda et al. ............ 128/207.15 |
| 4,674,495 | 6/1987 | Orr |
| 4,751,924 | 6/1988 | Hammerschmidt et al. |
| 4,762,125 | 8/1988 | Leiman et al. |
| 5,148,802 | 9/1992 | Sanders et al. ............ 128/204.23 |

OTHER PUBLICATIONS

Cress et al., "A Clinical Guide to Cardiopulmonary Medicine", 1989, Puritan-Bennett Corp., Kansas City, MO.
Adamo, et al., "The Cleveland Clinic's Initial Experience . . . Oxygen Therapy" *Respiratory Care*, vol. 35, No. 2, pp. 153-160 (Feb. 1990).
Goldstein, et al., "Super carbia in Children: Clinical Course and Outcome" *Critical Care Medicine*, vol. 18, No. 2, pp. 166-168 (Feb. 1990).
Hachenberg et al, "Constant-Flow Ventilation in . . . Pulmonary Emphysema" *Acta Anaesthesiol Scand*, vol. 33, pp. 416-421 (1989).
Sznajder et al., "Combination of Constant Flow . . . Pulmonary Edema" *Journal of Applied Physiology*, vol. 67, No. 2, pp. 817-823 (1989).
Benumot et al., "The Importance of Transtracheal . . . Difficult Airway" *Anesthesiology*, vol. 71, No. 5, pp. 769-778 (Nov. 1989).
Branditz et al., "Continuous Transtracheal Oxygen . . . Resuscitation" *Chest.*, vol. 95, No. 2, pp. 441-448 (Feb. 1989).
Frame et al., "Transtracheal Needle Catheter . . . Animal Model" *Annals of Emergency Medicine*, vol. 18, No. 2, pp. 127-133 (Feb. 1989).
Stewart, R., "Manual Translaryngeal Jet Ventilation" *Emergency Medicine Clinics at North America*, vol. 7, No. 1, pp. 155-164 (Feb. 1989).
Cote et al., "Cricothyroid Membrane Puncture: . . . Intravenous Catheter" *Critical Care Medicine*, vol. 16, No. 6, pp. 615-619 (1988).

(List continued on next page.)

Primary Examiner—Edgar S. Burr
Assistant Examiner—Kimberly L. Asher
Attorney, Agent, or Firm—Robert R. Meads

[57] ABSTRACT

A catheter system for ventilating patients experiencing severe respiratory distress. The system comprises a balloon-tip catheter, means for supplying a stream of oxygen gas at a controlled pressure and flow rate and means for rhythmically causing the balloon to expand and deflate when the catheter is inserted into the patient's trachea. Inflation of the balloon isolates the lower trachea so that a low pressure stream of oxygen flowing out from the distal tip of the catheter will expand the lungs and enter thereinto. When the balloon is deflated, the lungs collapse to discharge respiratory carbon dioxide. The unit is self-contained, and other than a source of oxygen, needs no other source of power to operate.

15 Claims, 2 Drawing Sheets

OTHER PUBLICATIONS

Odland et al., "Pneumothorax . . . Voice Prosthesis Use" *Annals of Otology, Rhinology & Laryngology*, vol. 97, No. 5, pp. 537–541 (Sep. 1988).

Vettermann et al., "Gas Exchange . . . During Continuous-Flow Ventilation" *J. Appl. Physiol.*, vol. 64, No. 5, pp. 1864–1869 (1988).

Long et al., "Constant Oxygen Insufflation (COI) in a Ventilatory Model" *Am. Rev. Res. Dis.*, vol. 138, pp. 630–635 (1988).

Cybulsky et al., "Contribution of Cardiogenic Oscillations . . . Ventilation" *J. Appl. Physiol.*, vol. 63, No. 2, pp. 564–570 (1987).

Slutsky et al., "Catheter Position and Blood Gases . . . Ventilation" *J. Appl. Physiol.* vol. 62, No. 2, pp. 513–519 (1987).

Kaufman et al., "Proximal Large-Bore Jet Ventilation . . . Surgery" *Arch Otolaryngol Head Neck Surg.*, vol. 113, pp. 314–320 (Mar. 1987).

Watson et al., "Effect of Flow Rate . . . Ventilation in Dogs" *Am. Rev. Respir. Dis.*, vol. 133, pp. 626–629 (1986).

Slutsky et al., "Trachael Insufflation of $O_2$ . . . Several Hours" *Anesthesiology*, vol. 63, No. 3, pp. 278–286 (Sep. 1985).

Smith et al., "Continuous Flow Apneic Ventilation" *Acta Anaesthesiol Scand*, vol. 28, pp. 631–639 (1984).

Drazen et al., "High-Frequency Ventilation" *Physiological Reviews*, vol. 64, No. 2, pp. 505–543 (Apr. 1984).

Fletcher et al., "A New Ventilator . . . High-Frequency Ventilation" *Respiration Physiology*, vol. 47, pp. 21–37 (1982).

Ngeow et al., "A New System for . . . High-Frequency Oscillation" *J. Appl. Physiol: Repirat. Environ. Exercise Physiol.*, vol. 53, No. 2, pp. 1638–1642 (1982).

Lehnert et al., "Constant-Flow Ventilation of Apneic Dogs" *J. Appl. Physiol.: Respirat. Environ. Exercise Physiol.*, vol. 53, pp. 483–489 (1982).

Froese et al., "High Frequency Ventilation" *Am. Rev. Res. Dis.*, vol. 123, pp. 249–250 (1981).

Goldstein et al., "$CO_2$ Elimination by High Frequency . . . Normal Subjets" *Am. Rev. Res. Dis.*, vol. 123, pp. 251–255 (1981).

Lyons et al, "The Airway Mechanics of Jet Ventilation" *Otolaryngol Head Neck Surg.*, vol. 89, pp. 364–369 (May 1981).

Bohn et al., "Ventilation by High Frequency Oscillation" *J. Appl. Physiol: Respirat. Environ. Exercise Physiol.*, vol. 48, No. 4, pp. 710–716 (1980).

Carden et al., "Precutaneous Jet Ventilation" *Ann. Otol.*, vol. 83, pp. 652–655 (1976).

Attia et al., "Transtracheal Ventilation" *JAMA*, vol. 234, No. 11, pp. 1152–1153 (Dec. 1975).

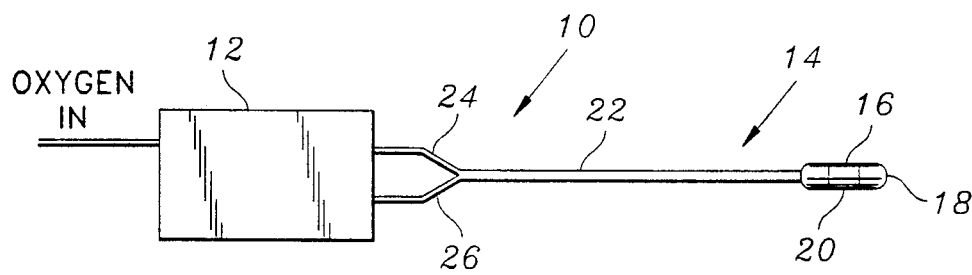
FIG. 1
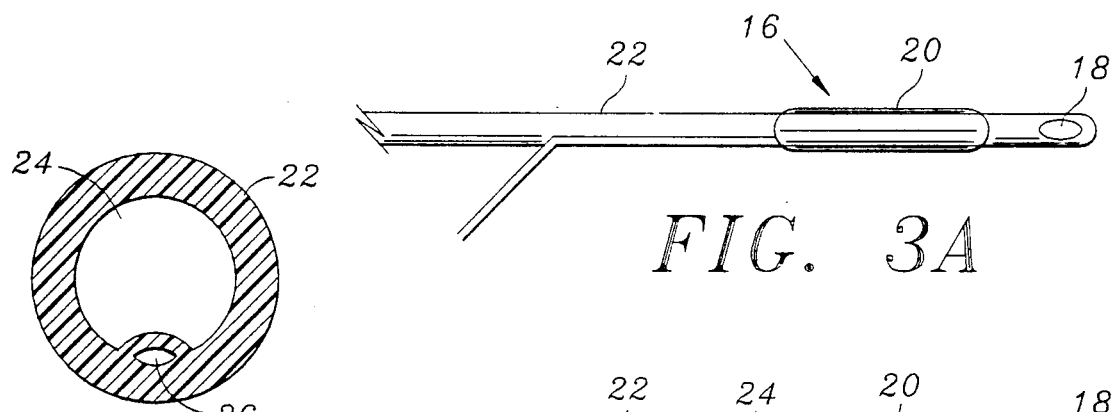
FIG. 2
FIG. 3A
FIG. 3B
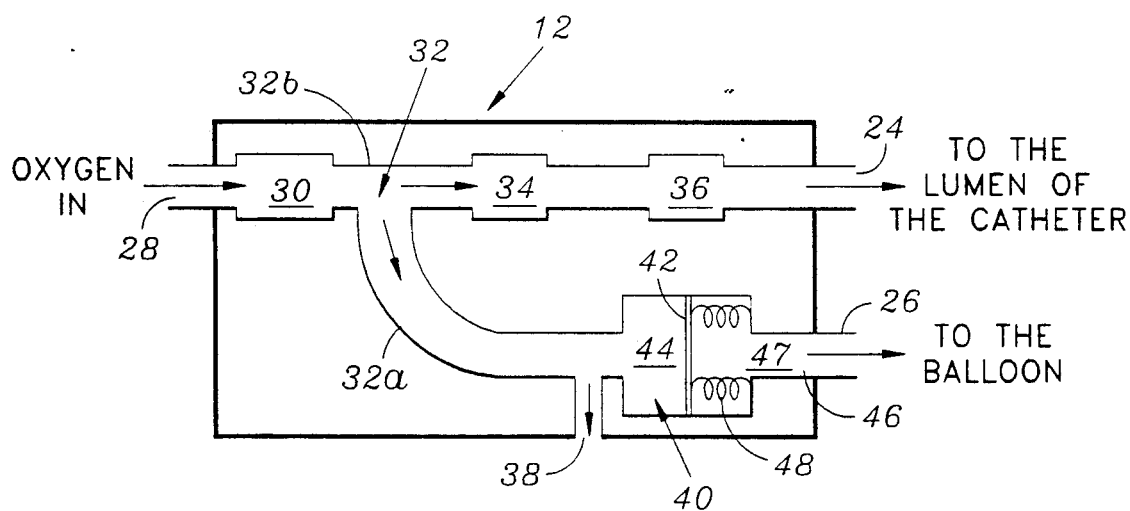
FIG. 4

BALLOON-TIPPED CATHETER VENTILATION SYSTEM AND METHOD FOR USING SAME HAVING RHYTHMICALLY INFLATED AND DEFLATED BALLOON

FIELD OF THE INVENTION

The present invention is related to the field of catheters used for ventilating patients having partially or completely blocked tracheal passages and more particularly to ventilation catheters having an integral inflatable balloon therewith.

BACKGROUND OF THE INVENTION

Medical and paramedical personnel engaged in the practice of emergency medicine and medical personnel in operating rooms and in intensive care units must be ready to face a broad spectrum of problems and challenges presented by traumatized patients. Particularly important is the ability of such medical personnel to respond to life threatening air passage blockage, injuries and diseases. Many of these conditions appear with little or no warning, and they must be dealt with immediately if further trauma is to be avoided. Often there is little or no time for consultation with an experienced specialist. For this reason, emergency room medical personnel are trained to quickly react to and treat air passage problems whenever and wherever they occur. In many cases, accident victims respond well to relatively simple basic maneuvers such as suction or positioning the head and jaws to free the oropharyngeal and nasopharyngeal areas from any gross obstructions which might be present. In still other cases positive pressure ventilation, such as the use of mouth-to-mouth breathing, or the use of various ectotracheal devices such as esophageal obturators, demand-mask or bagvalve-mask devices will suffice.

There are times, however, when the patient exhibits much more serious conditions, such as those in which large tumors or severe facial injuries partially or even totally block access to the upper trachea. When this happens, more advanced procedures are required. In many of these cases, the use of insufflation techniques such as orotracheal or nasotracheal intubulation coupled with the application of low pressure oxygen will provide sufficient ventilation. However, in those patients exhibiting massive facial trauma, or when there is either a laryngeal stenosis lying below the vocal cords or a major tracheal obstruction, such techniques often will not provide a level of ventilation adequate to prevent respiratory acidosis. In such situations, a number of alternate endotracheal techniques, such as cricothyroidotomy and tracheostomy have been described in the prior art; however, time, experienced personnel and specialized equipment are required to apply them. Further, even when appropriately applied, permanent scarring may result.

For the most drastic situations, two other methods have been described for emergency endotracheal airway management. These involve the delivery of oxygen to the lungs via a translaryngeal or transtracheal puncture and the use of a percutaneously placed catheter to provide either (1) continuous low-flow insufflation or (2) high pressure jet-flow ventilation. Problems reported with continuous low-flow insufflation are carbon dioxide retention and respiratory acidosis. While Jet ventilation produces better results, there is also a higher risk of pulmonary barotraumatic conditions such as the generation of excessive alveolar pressures. These, in turn, can either lead to alveolar rupture and subsequent leakage of lung gases into the pleural space, or the development of conditions such as mediastinal emphysema. Its use also requires skill and time for set up. Neither method should be used in situations where there is total airway obstruction. Also, there is no evidence that either technique provides adequate protection from problems resulting from the aspiration of throat secretions, blood or vomit.

SUMMARY OF THE INVENTION

The present invention comprises both a ventilation catheter system and a method for using same. In its broadest aspects, the catheter system comprises an oxygen carrying tracheal catheter having a balloon circumferentially attached at the distal end thereof, means for providing oxygen at a preselected low pressure and volumetric rate of flow to and through said catheter, and means for causing said balloon to rhythmically expand and contract. When the distal end of the catheter is placed within the lower trachea of a patient through the mouth and larynx or via a transtracheal puncture, the expansion of the balloon will block off the upper trachea and the pressure of the oxygen stream flowing from the catheter tube will enter and expand the lungs. Subsequent deflation of the balloon releases the oxygen pressure within the lungs, thus allowing them to collapse and expel respiratory carbon dioxide therefrom around the catheter. In the method of this invention, the tip of a small diameter, balloon-tip catheter is placed within the trachea and moved to a position which is just above carina, where the trachea branches into the lungs. At that time and place, rhythmic balloon activation is started to periodically inflate and deflate the balloon. Such activation results in the trachea being periodically blocked, with the lungs expanding to aerate the blood, and opened to allow the lungs to collapse and discharge respiratory carbon dioxide.

Provided that the upper trachea and larynx are not completely obstructed, discharged gases will flow along the outside of the catheter up through the larynx, whereupon they are vented from the mouth or nose as in normal breathing. If, however, the upper trachea is totally or severely obstructed, such venting can easily be accomplished through a second transtracheal catheter inserted to below the obstruction.

In the present invention, the use of a balloon-tip catheter, as described herein, both effectively blocks out external fluids and protects the airway from major tracheal damage and subglottic and glottic scarring, while the use of low pressure oxygen is an effective means for preventing barotrauma. In addition, the system, in general, and balloon actuation in particular, can be operated without either the need of an external electrical source or internal batteries, thus eliminating potential problems with sparking in an oxygen environment.

Other features and advantages of the invention will become apparent from the following description and accompanying drawings wherein are set, by way of illustration and example, certain embodiments of the present invention. The drawings constitute a part of the specification and include exemplary embodiments of the present invention, illustrating various features thereof.

BRIEF DESCRIPTION OF THE DRAWINGS

FIG. 1 is a schematic view of an exemplary balloon-tip catheter system of the present invention;

FIG. 2 is a cross sectional view of the dual channel flexible gas transfer tubing as used in the present invention;

FIGS. 3a and 3b are views of the distal end of a balloon-tip catheter as used in the present invention showing both the deflated and inflated conditions;

FIG. 4 is a schematic cross sectional view of an exemplary control module as used in the present invention;

DETAILED DESCRIPTION OF THE INVENTION

Figure 5:
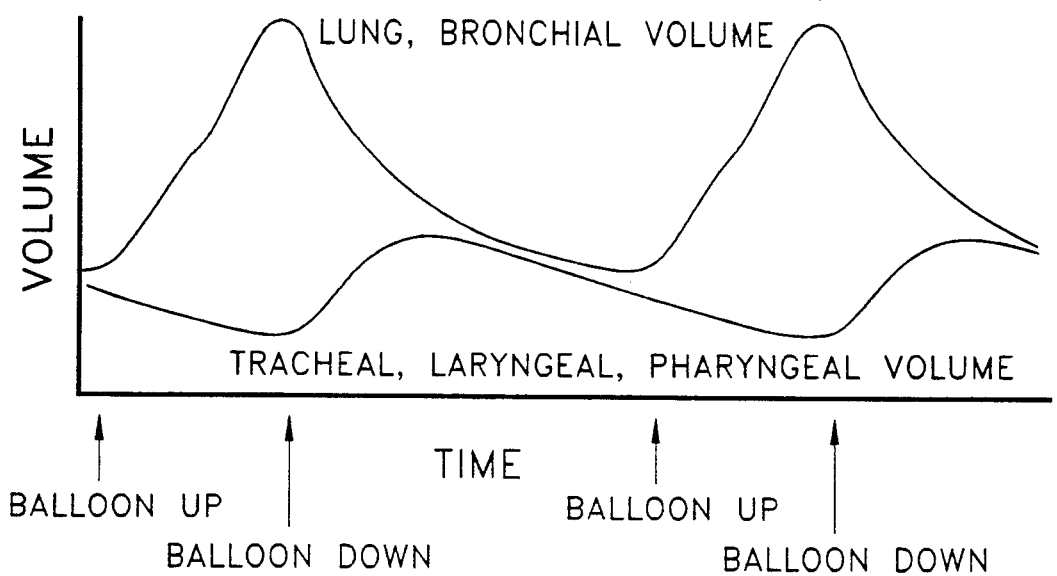
FIG. 5 is a graph showing proximal and distal airway volumes in a sedated dog when the balloon-tip catheter of FIG. 3 is used.

The present invention is a ventilation catheter system and a method of using same. FIG. 1 is a schematic view of an exemplary catheter system 10. As shown therein, system 10 comprises an actuation subsystem 12 and a balloon-tip catheter 14 comprising a distal end portion 16 having an open tip 18. A balloon 20 is positioned circumferentially around the distal end portion 16, a short distance to the rear of open tip 18. When the balloon 20 is inflated (FIG. 3b), it serves to block off and isolate the lower trachea so that the pressure of the oxygen flowing through distal end portion 16 will expand the lungs and aerate the blood. When balloon 20 is deflated (FIG. 3a), the release of this oxygen pressure causes the lungs to naturally collapse, with respiratory carbon dioxide therein being discharged. Both balloon 20 and distal end portion 16 are connected to actuation subsystem 12 by a flexible dual channel tube 22. A typical cross sectional view of such tubing is shown as FIG. 2. As shown therein, flexible tube 22 comprises a major interior channel 24 and a minor channel 26. As will be explained in more detail below, major channel 24 is connected to the distal end portion 16 and serves as the oxygen conduit thereto, while minor channel 26 carries the working fluid such as air which accomplishes balloon inflation.

Balloon-tip catheters, as used in the present invention, are formed of a inert bio-compatible material such as a silastic. Usually, such catheters are between about 30 and 40 cm in total length and about 3-5 mm in diameter. In the present invention, the flexible tube 22 preferably is about 3 mm in diameter, with the major oxygen flow channel 24 therein having an inside diameter of about 2 mm. This is sufficient to allow easy placement of the tip 18 of distal end portion 16 close to the carina, where the trachea branches into the bronchial passages of the lungs. By so doing, "dead" space within the upper trachea is minimized and the amount of oxygen flowing into the lungs is maximized.

In a balloon-tip catheter, as shown in FIGS. 3a and 3b, balloon 20 is a thin walled elongated cuff fitted circumferentially around and sealed at its ends to the external periphery of distal end portion 16. While balloon cuffs up to about 10 cm in length have been proposed for improved ventilation, the cuff is typically about 3 cm in length and it is positioned about 2 cm from the open end 18. Balloon materials are normally inert elastomers such as silicone rubber, although other elastomeric materials could be used.

In operation with subsystem 12, complete blockage of the trachea is achieved when balloon 20 is inflated to a diameter which is between about 2 to about 3 times that exhibited in its deflated condition. However, where it is desired to prevent such an expansion within the trachea, such as would be the case when the present invention is used with children or with patients exhibiting substantial tracheal trauma, transverse fibers can be embedded within the elastomer to limit the maximum possible balloon expansion to somewhat less than this.

A schematic depiction of subsystem 12 is shown as FIG. 4. In practice, the subsystem 12 may comprise a two piece housing which may be disassembled for sterilization and which includes passageways and chambers formed by the mating pieces of the housing to define oxygen manifolds and support chambers for the regulators, valves and replaceable spring loaded diaphragms mounted therein all as hereinafter described. The subsystem 12 is used in conjunction with an attached oxygen delivery system (not shown), which may either be a standard 55 psi hospital oxygen supply or, when field operations are involved, a tank of high pressure oxygen. In either case, it is most important that the oxygen pressure supplied to a patient be carefully controlled to avoid the possibility of barotrauma. Consequently, a manifold 28 has at its inlet end a conventional programmable pressure regulator 30 to reduce the oxygen pressure to below about 15 psi, preferably to below about 10 psi and, most preferably to about 5 psi. A manifold splitter 32 divides such low pressure oxygen stream into branches 32a and 32b. In branch 32a, a minor portion of the gas is diverted to actuate balloon 20, with the remaining major portion of the oxygen gas stream flowing in branch 32b through a conventional programmable flow regulator 34. The flow regulator 34 is set to limit the flow rate of oxygen to a selected predetermined maximum value and introduces an additional pressure drop reducing the pressure of the oxygen leaving the regulator 34 to below 100 cm $H_2O$ (approximately 1.5 psi) and preferably between 30-50 cm $H_2O$. Typically, the flow rate will range between about 5 and about 15 liters/minute, depending upon the size of the patient and the needs generated by his or her injuries. The oxygen gas stream next enters a pressure safety valve 36 having an operating range of about 20 to 100 cm $H_2O$. In the event of a failure of pressure regulator 30 or any undesired increase in oxygen pressure, the safety valve 36 will prevent the patient from being exposed to gas pressures in excess of 100 cm $H_2O$. From the safety valve 36, the low pressure gas enters the major channel 24 in flexible tube 22 through which it flows to opening 18 of catheter end portion 16 and then out into the trachea as described above.

As previously noted, control of the rhythmic inflation and deflation of balloon 20 is accomplished within manifold branch 32a. In the embodiment illustrated in FIG. 4, branch 32a comprises, in combination, a blow hole 38 and a balloon actuator 40. Actuator 40, in turn, is divided by a flexible impermeable diaphragm 42 into a pressure actuator chamber 44 and a pressure transfer chamber 46. Associated with diaphragm 42 within transfer chamber 46 is a compression means 48, typically a spring. Attached to the outlet of chamber 46 is minor channel 26 of flexible tube 22 which, in turn, leads to balloon 20. The pressure transfer chamber 46 and minor channel 26 contain air 47. When blow hole 38 is in the open condition shown, most of the oxygen flowing in manifold channel 32a is discharged through blow hole 38 to the atmosphere with any pressure generated on diaphragm 42 being insufficient to overcome the resistance of compression means 48, so balloon 20 remains deflated. In this situation, while oxygen will continuously flow into the trachea, the low pressure caused by a back flow of at least part of the oxygen up the trachea creates a situation wherein the residual oxygen pressure is insufficient to expand the lungs. However, when blow hole 38 is blocked off, the oxygen flowing into branch 38a remains confined within actuator chamber 44, developing on diaphragm 42 a static pressure equal to that established by regulator 30 (e.g. 5-15 psi). This relatively high pressure (when compared to the 1.5 psi or less pressure of the oxygen supplied to the distal end 16 of the catheter) acts to overcome the opposing resistance of compression means 48 and, as a result, diaphragm 42 is displaced distally.

Such diaphragm displacement forces the air 47 contained within balloon actuator chamber 42 and minor channel 26 in flexible tube 22 and into the balloon 20 to inflate the balloon 20. As shown, the fluid path in the balloon actuation system is closed and once it is assembled, no other sources of the pressurizing fluid are required.

Once the balloon 20 is inflated, the entire pressure of the oxygen in branch 32b is now exerted on the lungs and they expand to allow the flowing oxygen to enter thereinto. Then, when blow hole 38 is unblocked, the static pressure on diaphragm 42 is now relieved, compression means 48 returns diaphragm 42 back to its normal "open" position, and the natural elasticity of balloon 20 will force the air 47 back into the reservoir chamber 46 and channel 26 and allow the balloon to deflate. This opens up the tracheal passages for carbon dioxide discharge. Note that no outside source of power is required to generate the forces causing balloon 20 to inflate or deflate. Both of these actions are precipitated simply by providing for the presence or absence of a gas pressure on diaphragm 42. Typical proximal and distal airway volumes observed when the apparatus of the present invention is used on a sedated dog are illustrated in FIG. 5.

Figure 6:
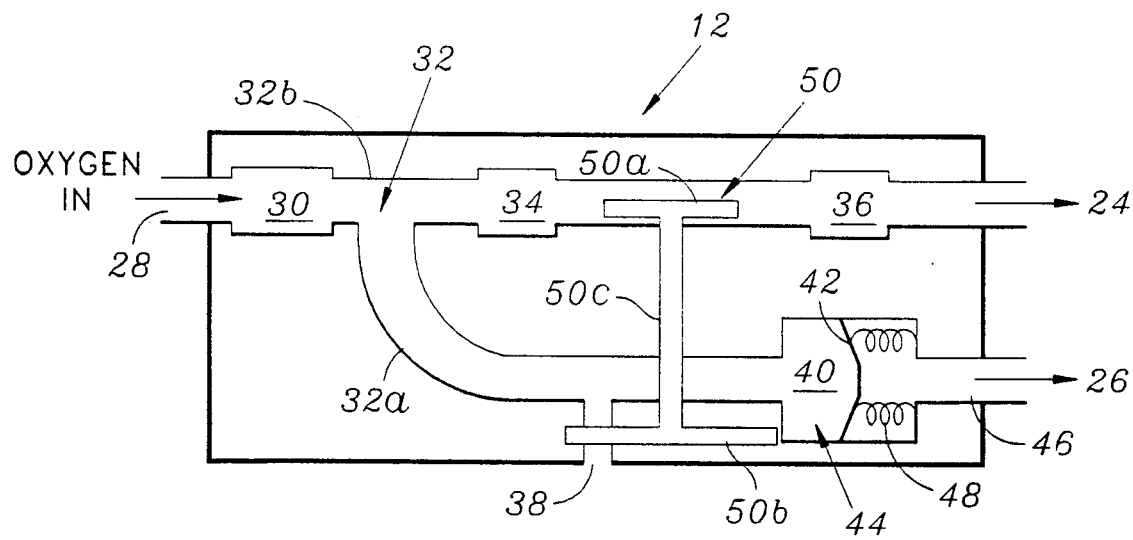
FIG. 6 is a schematic cross sectional view of a second embodiment of the exemplary control module of FIG. 4.
Figure 7:
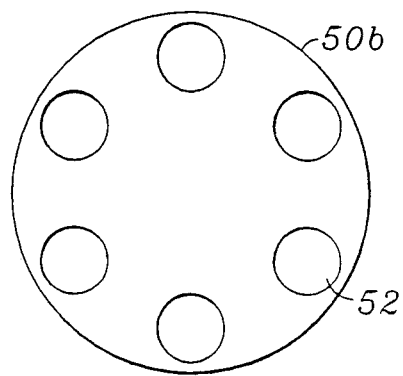
FIG. 7 is a plan view of a rotor disc used in the embodiment shown in FIG. 6.

For a system to be useful in ventilating patients, it is most important that the carbon dioxide within the lungs be discharged on a regular or periodic basis, i.e. the system should simulate regular breathing. In an embodiment of the present invention, one means for accomplishing such rhythmic simulation is shown diagrammatically in FIG. 6. As there illustrated, actuation system 12 further comprises a turbine driven rotor assembly 50 comprising a turbine 50A and a rotor disc 50B connected to the turbine by a shaft 50C. The turbine 50A is mounted for turning in the branch 32b between the regulator 34 and the valve 36 in response to oxygen flowing in the branch 32b. As shown in FIG. 7, the rotor disc 50B contains a plurality of circumferentially spaced holes 52 for consecutively aligning with the blow hole 38 as the rotor turns with the turbine in response to oxygen flow in the branch 32b. Such alternate opening and closing of the blow hole 38 in FIG. 6 controllably inflates and deflates the balloon to effect a breathing by the patient. Normal breathing rates for most people are between about 10 and about 30 times/minute. Since the use of pure oxygen involves aerating the patient with a higher than normal concentration of oxygen, the width and number of holes in rotor disc 50B are established to allow balloon 20 to remain inflated (inhalation) for a time which is typically about 2-3 times as long as it is deflated (exhalation) as the disc rotates. Such operation helps prevent respiratory acidosis by allowing more than sufficient time for full evacuation of the lung gasses during exhalation. Once the system of the present invention is attached to an oxygen source and inserted into the trachea, merely causing the oxygen to flow through manifold 28 will automatically establish the rhythmic balloon actuation described above. Such an ability is of particular importance in emergency situations.

It should be appreciated that other programmable means may be used to set the breathing rhythm with balloon 20. It also should be appreciated that other components may be included as a part of the apparatus of the present invention, such as pressure and flow rate gauges and flow line check valves to prevent any possible contamination of the oxygen with exhaled carbon dioxide. Further, in the turbine configuration of FIG. 6, the rotor disc 50B may be connected to the turbine 50A via a reduction gear assembly if improved mechanical advantage is desired for a turning of the disc in response to a turning of the turbine.

The invention is further illustrated by the following examples, which are illustrative of a specific mode of practicing the invention and not intended to limit its scope.

EXAMPLES

In all the following examples, a single healthy 16 KG adult male beagle was used. At the start of each test, the dog was intramuscularly premedicated with acepromazine (1.1 mg/kg) and atropine (1 cc), after which an intravenous line was established and the dog anesthetized with sodium pentobarbital (25 mg/kg). Paralysis was then achieved with initial administration of panacuronium (0.3 mg/kg), with paralysis being maintained by the administration of an additional 0.15 mg/kg every half hour. The dog was intubated and ventilated with a mechanical ventilator of conventional design. Electrocardiographic monitoring was established, along with the placement of a femoral arterial line for the continuous monitoring of blood pressure and for drawing arterial blood gas (ABG) samples, with samples being taken about every 15 minutes. Hydration was maintained throughout the procedure with the intravenous administration of lactated Ringers solution at about 30 cc/hour (enough to keep the vein open). Prior to the start of the procedure, the dog was placed on a heating pad and the rectal temperature was monitored continuously.

After stabilization on the ventilator at a rate of 30 ventilations per minute with an oxygen tidal volume of about 200 cc, the endotracheal tube was removed and replaced with a 12, 14 or 16 French Foley balloon-tip catheter with the open distal end thereof being advanced to just above the carina where the trachea separates to enter the bronchial passages. The maximum airway oxygen pressure was set at about 30 cm of water by adjusting the pressure release valve on the anesthesia tubing according to the pressure reading from the anesthesia machine. In all of the test procedures described below, cycling of the Foley catheter balloon was performed with the oxygen flow rate set between about 5 to about 8 liters/minute at a pressure of about 20-30 cm $H_2O$.

EXAMPLE 1

The dog was prepared according to the general procedure described above. After stabilization had been achieved, balloon cycling was started at 50 cycles/minute with an inflation/deflation time ratio of 3:1. While an oxygen rate of about 8 liters/minute was maintained throughout, minimal chest motion was observed and after about 15 minutes, the partial pressure carbon dioxide in the dog's blood rose from about 30 mm Hg to 46 mm Hg. The ventilation rate was then reduced to about 30 cycles/minute with chest motion being improved and the carbon dioxide partial pressure showing a moderate improvement by dropping, over the next 15 minutes, to about 35 mm Hg. At ninety minutes, the oxygen rate was lowered to about 6 liters/minute which resulted in a slight increase in the carbon dioxide partial pressure. At the conclusion of the test, the dog was awakened and returned to the animal care facilities with no obvious signs of tracheal trauma or other injury.

This test showed that in the absence of any simulated or actual trauma, the method of the present invention was able to maintain near normal respiration when used as described hereinabove. The bloodstream oxygen partial pressure level ranged from about 551 to about 673 mm Hg during this procedure. FIG. 5 is a schematic showing of relative changes in proximal and distal airway volumes over time.

EXAMPLE 2

Eight days after the completion of the test procedure in Example 1, the dog was prepared as described above and the procedure started at an oxygen flow rate of about 8 liters/minute and a balloon cycling rate of about 30 cycles/minute. The initial partial pressure of carbon dioxide was about 22 mm Hg and although decreasing to about 20 mm HG after 15 minutes of cycling, it had increased to about 25 mm after 30 minutes, at which time the oxygen flow rate was decreased to about 5 liters/minute and the balloon cycling rate lowered to about 20 cycles/minute. Under these conditions, the carbon dioxide level remained essentially constant. After an additional 30 minutes of operation at these levels, the oxygen rate was increased back to about 8 liters/minute and the balloon cycling was stopped with the balloon in the deflated position. After about 45 minutes, the carbon dioxide level in the bloodstream had about doubled, at which time balloon cycling was resumed. After an additional 20 minutes of cycling, the hypercapnia (high blood $CO_2$ levels) was substantially reversed with the difference in the carbon dioxide level increase which had occurred between the stopping and restarting of balloon cycling being reduced by about half to normal levels. The bloodstream oxygen level ranged from a partial pressure of 545 mm HG to one of about 647 during the procedure. With the conclusion of this test, the dog was once again reawakened and returned to the animal care facilities.

This test showed that without the balloon cycling feature of the present invention, the mere introduction of oxygen into the lungs, in and of itself, is inadequate to provide proper ventilation and carbon dioxide removal.

EXAMPLE 3

Seventeen days after the completion of the procedure described in Example 2, the dog was prepared as described above The test procedure was started with an oxygen flow rate of about 8 liters/minute and a balloon cycling rate of about 30 cycles/minute. The initial carbon dioxide partial pressure in the bloodstream was about 32 mm Hg and after about 15 minutes it had decreased to about 25 mm Hg. At this time the oxygen flow rate was reduced to about 5 liters/minute with the carbon dioxide level rising slightly over the next 30 minutes of testing. After 45 minutes, a 14 gauge cannula was inserted percutaneously into the trachea and near-total airway obstruction simulated by tightly packing the hypopharynx with wet gauze. The bloodstream carbon dioxide level rose only slightly during the next 30 minutes of testing. After 75 minutes had passed, the oxygen flow rate was increased back to 8 liters/minute with a slight drop in blood stream carbon dioxide levels resulting therefrom.

After about 2 hours total of testing, the hypopharyngeal packing was removed. Fifteen minutes later, a bag of normal saline solution was connected to the 14 gage cannula and a total of about 90 cc of solution was then dripped into the proximal trachea over the next 15 minutes. As shown by a bloodstream carbon dioxide level of about 35 mm Hg after a total of two hours 40 minutes of testing and an oxygen partial pressure range of between about 553 and about 643 mm Hg, it could be concluded that there was essentially no affect on either the carbon dioxide elimination or the rate of oxygenation.

Upon completion of this third test, the dog was euthanized and the trachea surgically removed. An eyeball examination of the tissues showed no signs of obvious irritation even after a total of about 6.5 hours ventilation. A histological examination basically confirmed this observation.

This third test showed that the method of the present invention as safe and effective in providing adequate lung ventilation even when the tracheal passage was essentially completely blocked and/or when extraneous fluid had dripped into the bronchial passages.

Thus it has been shown that the apparatus and method of the present invention have overcome the limitations observed with prior art practices for treating severe airway trauma conditions. In particular, the use of low pressure oxygen flow rates is effective in preventing barotrauma. Further, the ability to use relatively small catheters will enable the practician to have better access to the upper trachea and the larynx, where surgical procedures at these locations are required. The use of small catheters, as applied herewith, reduces the difficulty in responding to and effectively treating problems relating to severely obstructed airways. Further, these can be easily placed or replaced by non-skilled personnel and the system can even be used in an ambulatory setting when necessary. Furthermore, operation of the system can be accomplished without creating any possible sparking hazard.

While particular embodiments of the invention have been described, it will be appreciated and understood that the invention is not limited thereto. Many obvious variations and modifications can be made and are intended to be within the scope of the present invention as defined by the appended claims.

Having now described my invention, I claim:

1. A ventilation catheter system comprising:
   a hollow catheter having a balloon circumferentially attached to a distal end thereof for placement in a trachea of a patient;
   means receiving a stream of oxygen from a supply source for continuously flowing oxygen at a constant relatively low pressure through the distal end of the catheter and into the patient's trachea during both inhalation and exhalation portions of the patient's breathing cycle; and means responsive to the oxygen stream from the source for (a) rhythmically inflating the balloon to block the trachea such that the continuous flow of low pressure oxygen through the distal end of the catheter expands the patient's lungs during the inhalation portion of the patient's breathing cycle and (b) rhythmically deflating the balloon to unblock the trachea such that respiratory carbon dioxide is expelled from the patient's lungs around the catheter and deflated balloon and outward through the trachea during the exhalation portion of the patient's breathing cycle and while the flow of low pressure oxygen continues inward through the distal end of the catheter and into the trachea wherein said means for rhythmically inflating and deflating the balloon comprises means for diverting a minor portion of said stream to inflate and deflate said balloon, said minor portion of said stream being at a controlled relatively high pressure.

2. The ventilation catheter system of claim 1 wherein said oxygen stream receiving means comprises a manifold receiving said oxygen stream, said manifold further comprising a programmable pressure regulator and a programmable flow rate regulator for controlling the pressure and rate of flow of oxygen into the distal end of the catheter.

3. The ventilation catheter system of claim 1 further comprising actuator means for periodically inflating and deflating said balloon in response to the minor portion of said stream, wherein said means for rhythmically inflating and deflating the balloon comprises means for directing said minor portion of said stream of oxygen at a controlled relatively high pressure alternately through an opening to the atmosphere and to said actuator means.

4. The ventilation catheter system of claim 3 wherein the actuator means comprises a pressure actuator chamber and a pressure transfer chamber divided by a spring loaded diaphragm, the pressure actuator chamber receiving the minor portion of said oxygen stream to periodically exert a pressure on and periodically move the diaphragm toward the pressure transfer chamber to periodically drive a working fluid into the balloon to periodically inflate and deflate the balloon.

5. The ventilation catheter system of claim 4 wherein said means for rhythmically inflating and deflating the balloon further comprises a turbine responsive to the stream of oxygen to turn a rotor disc having openings therein for periodically venting to atmosphere the portion of the oxygen stream whereby the pressure is periodically generated and released in the pressure actuator chamber so that the balloon automatically inflates and then deflates as the turbine is activated.

6. The ventilation catheter system of claim 5 wherein the openings in the rotor disc are spaced relative to a vent to cause the balloon to be inflated for about 2 to 3 times as long as it is deflated as the disc turns with the turbine.

7. The ventilation catheter system of claim 3 wherein the pressure of oxygen supplied to the distal end portion of the catheter is less than about 1.5 psi and the pressure of the portion of the stream of oxygen applied to the actuator means is between 5 and 15 psi.

8. The ventilation catheter system of claim 3 wherein the controlled flow rate of oxygen to the distal end of the catheter is between about 5 and about 15 liters per minute.

9. The ventilation catheter system of claim 8 wherein said balloon is inflated between about 10 and about 40 times per minute.

10. The ventilation catheter system of claim 1 wherein the pressure of the oxygen supplied to the distal end portion of the catheter is less than about 1.5 psi.

11. A method for simulating breathing in a patient with a balloon-tipped catheter, said method comprising the steps of:

(a) providing a catheter and a source of oxygen;
(b) attaching said catheter to said source of oxygen;
(c) placing a distal end of the catheter in a trachea of said patient;
(d) continuously flowing oxygen from the source at a controlled, constant, relatively low pressure through said distal end into the trachea; and
(e) providing balloon actuating means;
(f) diverting a minor portion of the stream of oxygen and flowing said minor portion of said stream of oxygen from the source at a controlled, relatively high pressure periodically between the atmosphere and said balloon actuating means (1) to rhythmically inflate the balloon to block the trachea while the continuous flow of low pressure oxygen through the distal end of the catheter expands the patient's lungs and (2) to rhythmically deflate the balloon to unblock the trachea and expel respiratory carbon dioxide from the patient's expanded lungs around the catheter and deflated balloon and outward through the trachea while the flow of low pressure oxygen continues inward through the distal end of the catheter and into the trachea.

12. The method of claim 11 further comprising the step of controlling the pressure of oxygen flowing through the distal end of the catheter and into the trachea to be less than about 1.5 psi.

13. The method of claim 12 further comprising the step of controlling the pressure of the oxygen flowing periodically between atmosphere and balloon actuating means to be between about 5 psi and about 15 psi.

14. The method of claim 13 further comprising the step of controlling the flow of oxygen into the trachea to be between about 5 and about 15 liters per minute.

15. The method of claim 13 further comprising the step of controlling the rhythmic inflating of the balloon to between about 10 and about 40 times per minute.

* * * * *